(12) United States Patent
Kokane et al.

(10) Patent No.: US 8,946,414 B2
(45) Date of Patent: Feb. 3, 2015

(54) PROCESSES FOR THE PREPARATION OF DIPYRIDAMOLE

(75) Inventors: Dattatrey Kokane, Panvel (IN); Bindu Manojkumar, Panvel (IN); Vinayak Govind Gore, Panvel (IN)

(73) Assignee: Generics [UK] Limited, Hertfordshire (GB)

( * ) Notice: Subject to any disclaimer, the term of this patent is extended or adjusted under 35 U.S.C. 154(b) by 146 days.

(21) Appl. No.: 13/700,845

(22) PCT Filed: May 31, 2011

(86) PCT No.: PCT/GB2011/051023
§ 371 (c)(1),
(2), (4) Date: Feb. 25, 2013

(87) PCT Pub. No.: WO2011/151640
PCT Pub. Date: Dec. 8, 2011

(65) Prior Publication Data
US 2013/0172369 A1    Jul. 4, 2013

(30) Foreign Application Priority Data
May 31, 2010   (IN) .......................... 1655/MUM/2010

(51) Int. Cl.
C07D 487/00    (2006.01)
C07D 491/00    (2006.01)
C07D 487/04    (2006.01)

(52) U.S. Cl.
CPC .................................. *C07D 487/04* (2013.01)
USPC ....................................................... 544/256

(58) Field of Classification Search
None
See application file for complete search history.

(56) References Cited

U.S. PATENT DOCUMENTS 3,031,450 A    4/1962   Fischer et al.

FOREIGN PATENT DOCUMENTS

| DE | 18 12 918 A1 | 11/1969 |
| DE | 117456 | 2/1975 |
| DE | 115670 | 10/1975 |
| DE | 2927539 | 1/1981 |
| RO | 104718 | 9/1994 |
| WO | WO 2007/080463 | 7/2007 |

OTHER PUBLICATIONS

Curtin, Nicola J. et al. "Resistance-Modifying Agents of Pyrimido[5,4-*d*]pyrimidine Modulators of Antitumor Drug Activity. Synthesis and Structure-Activity Relationships for Nucleoside Transport Inhibition and Binding to $\alpha_1$-Acid Glycoprotein", Journal of Medicinal Chemistry, 2004, vol. 47, No. 20, Aug. 26, 2004, pp. 4905-4922.
International Search Report from PCT/GB2011/051023, mailed Sep. 26, 2011, 4 pages.
International Preliminary Report on Patentability from related PCT Application PCT/GB2011/051023, dated Dec. 4, 2012, 10 pages.

*Primary Examiner* — Jeffrey H Murray
(74) *Attorney, Agent, or Firm* — Fulbright & Jaworski LLP; Scott D. Rothenberger

(57) ABSTRACT

The present invention relates to the active pharmaceutical ingredient dipyridamole. In particular, it relates to efficient processes for the preparation of dipyridamole which are amenable to large scale commercial production and provide the required product with improved yield and purity. The present invention also relates to a novel crystallization method for the purification of dipyridamole.

11 Claims, 1 Drawing Sheet

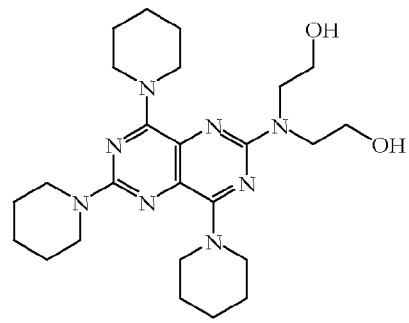
Impurity A
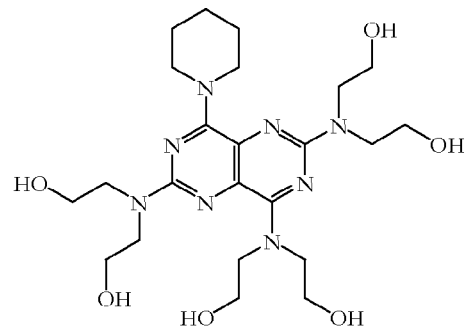
Impurity B
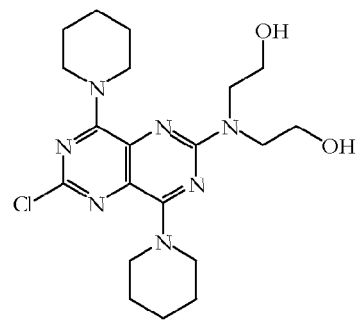
Impurity C
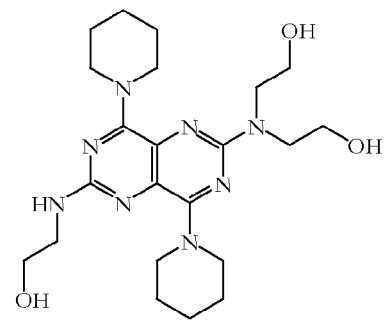
Impurity D
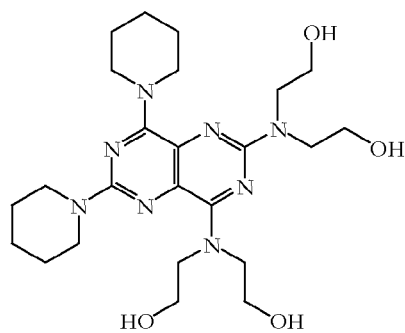
Impurity E
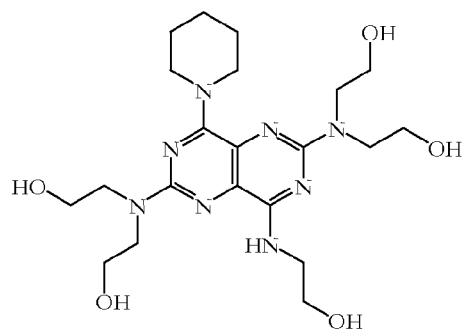
Impurity F
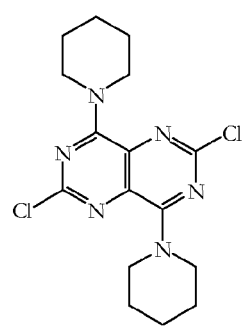
Impurity G

PROCESSES FOR THE PREPARATION OF DIPYRIDAMOLE

CROSS-REFERENCE TO RELATED APPLICATIONS

This application is a Section 371 National Stage Application of International No. PCT/GB2011/051023, filed May 31, 2011, and published as WO 2011/151640 on Dec. 8, 2011, which claims priority from the India Application 1655/MUM/2010, filed May 31, 2010, the contents of which are incorporated herein in their entirety for all purposes.

FIELD OF THE INVENTION

The present invention relates to the active pharmaceutical ingredient dipyridamole. In particular, it relates to efficient processes for the preparation of dipyridamole which are amenable to large scale commercial production and provide the required product with improved yield and purity. The present invention also relates to a novel crystallization method for the purification of dipyridamole.

BACKGROUND OF THE INVENTION

Dipyridamole, represented by structural formula (I), possesses platelet aggregation inhibiting, anti-thrombotic and vasodilator properties and it is marketed as an anti-platelet therapy for the treatment and prevention of disorders such as thrombo-embolisms.

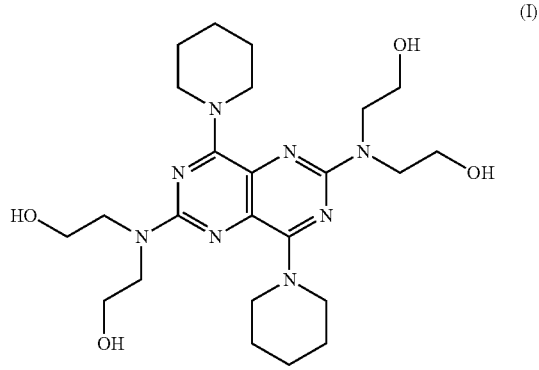 [SMILES: OCCN(CCO)c1nc(N2CCCCC2)c2nc(N(CCO)CCO)nc(N3CCCCC3)c2n1]

(I)

A process for the preparation of dipyridamole, disclosed in patent U.S. Pat. No. 3,031,450, involves the reaction of 2,6-dichloro-4,8-dipiperidino-pyrimido(5,4-d)pyrimidine with diethanolamine (see Scheme 1). The preparation of 2,6-dichloro-4,8-dipiperidino-pyrimido(5,4-d)pyrimidine is also reported in U.S. Pat. No. 3,031,450 and is incorporated herein by reference. The reaction to prepare dipyridamole does not employ an additional reaction solvent and is a neat mixture of the two reactants carried out at a very high temperature of 190 to 195° C. The process also involves a cumbersome work-up to isolate dipyridamole, since the crude product obtained is a pasty mass which needs decantation of the mother liquor and further purification. This decantation process is not practical on commercial scale.

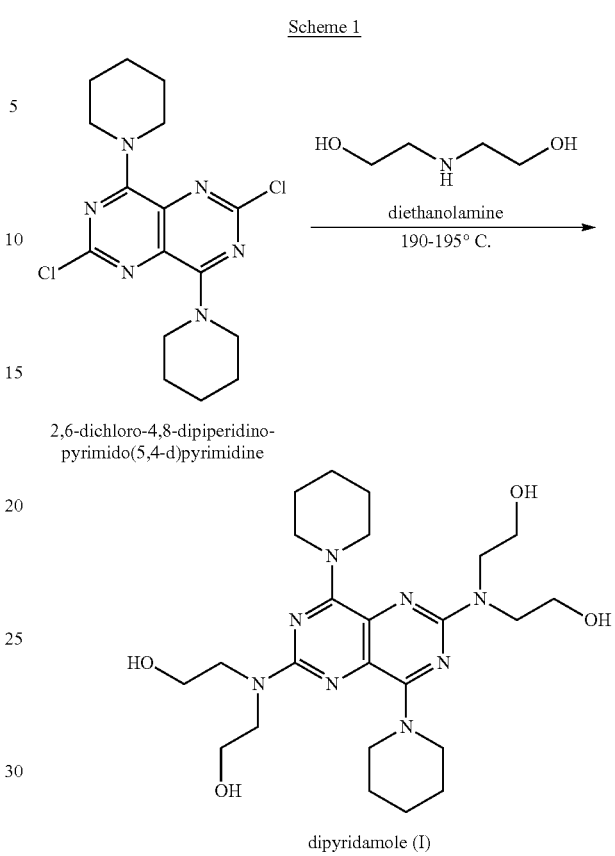

Scheme 1

2,6-dichloro-4,8-dipiperidino-pyrimido(5,4-d)pyrimidine dipyridamole (I)

A similar process for the production of dipyridamole is described in patent DD 117456 wherein the reaction conditions exemplified are heating 2,6-dichloro-4,8-dipiperidino-pyrimido(5,4-d)pyrimidine and diethanolamine at 155 to 160° C. under vacuum. However, this process again requires a high temperature which leads to the formation of impurities.

A process for the preparation and purification of dipyridamole is disclosed in patent DE 1812918, wherein 2,6-dichloro-4,8-dipiperidino-pyrimido(5,4-d)pyrimidine and diethanolamine are heated to 150 to 200° C. After completion of the reaction, the reaction mixture is dissolved in chloroform, which is further separated into an upper layer of diethanolamine and its hydrochloride and a chloroform solution. The chloroform solution obtained is separated and reduced to dryness after stirring with water. This process also requires a high temperature which can lead to the formation of impurities. In addition, the solvent used for the isolation of dipyridamole, chloroform, is inconvenient as it is a restricted solvent and its permitted limit in the final marketed dipyridamole is very low.

A similar process, wherein dipyridamole is manufactured by the reaction of diethanolamine with 2,6-dichloro-4,8-dipiperidino-pyrimido(5,4-d)pyrimidine is disclosed in patent RO 104718. However, this process again requires high temperatures of 180 to 200° C. which leads to the formation of impurities and, consequently, the yield of the final product is very low (58%) with a purity of less than 98%.

A process is disclosed in patent DD 115670, wherein the purification of dipyridamole involves refluxing it in butyl acetate, AcOBu, for 2 hours in the presence of an equal amount of silica gel or column chromatography on silica gel at 60-100° C. However, purification by column chromatography is not economical and not feasible on industrial scale. Moreover, this purification process only removes one specific impurity, 2,4,6-tris-(diethanolamino)-8-piperidino-pyrimido (5,4-d)pyrimidine.

The processes described above to prepare dipyridamole do not employ an additional reaction solvent but involve neat mixtures of the two reactants, 2,6-dichloro-4,8-dipiperidino-pyrimido(5,4-d)pyrimidine and diethanolamine, which are heated at very high temperatures. The use of neat reaction mixtures and/or high temperatures means that it is very difficult to control the levels of impurities formed.

Another process for the preparation of dipyridamole, disclosed in patent application WO 2007/080463, involves reacting diethanolamine with 2,6-dichloro-4,8-dipiperidino-pyrimido(5,4-d)pyrimidine in a solvent selected from the group consisting of 1-methyl-2-pyrrolidinone, sulpholane and polyethylene glycol. However, the exemplified reaction temperatures are very high at 190 to 200° C. and the HPLC purity of the crude dipyridamole is reported to be only 90-94%. A purification method is disclosed using first a ketonic solvent and then an alcohol and water. Even though the process disclosed in this patent application uses a solvent in the reaction, the temperature of reaction is still very high and the purification in ketonic solvent is reported at high temperature (100 to 120° C.). The HPLC purity after purification is reported as only 99.0-99.5%.

As discussed above, all the processes disclosed in the prior art for the preparation of dipyridamole suffer from serious disadvantages with respect to commercial production. The prior art synthetic and purification processes employ high temperatures in the preparation of dipyridamole which leads to inefficiency and high processing costs. The high temperatures also lead to higher levels of impurities being formed during manufacture with the consequence that further cumbersome and expensive purification procedures are required.

Considering the importance gained by dipyridamole as a commercial medicine, there is a great need for developing simple, inexpensive, good yielding and commercially feasible processes for the manufacture of high quality dipyridamole.

OBJECT OF THE INVENTION

Therefore there is a need for improved processes for the synthesis and purification of dipyridamole which provide commercial quantities of dipyridamole conveniently, economically and with high yield and purity. A further objective is to provide extremely pure dipyridamole substantially free of all impurities.

SUMMARY OF THE INVENTION

The term 'dipyridamole' as used herein throughout the description and claims means dipyridamole and/or any salt, solvate or isomer thereof unless specified otherwise.

A first aspect of the present invention provides a process for the preparation of dipyridamole comprising reacting 2,6-dichloro-4,8-dipiperidino-pyrimido(5,4-d)pyrimidine with diethanolamine at a temperature below 130° C., preferably below 125° C. Preferably the reaction temperature is between about 100° C. and below 130° C., preferably between about 100° C. and about 125° C., preferably between about 110° C. and about 125° C., preferably between about 110° C. and about 120° C., preferably between about 110° C. and about 115° C., and most preferably between about 113° C. and about 115° C.

Preferably, in a process according to the first aspect of the present invention, the reaction mixture is a neat mixture of the two reactants, 2,6-dichloro-4,8-dipiperidino-pyrimido(5,4-d)pyrimidine and diethanolamine, with no additional reaction solvent. Preferably the 2,6-dichloro-4,8-dipiperidino-pyrimido(5,4-d)pyrimidine is dissolved in the diethanolamine.

Alternatively, in a process according to the first aspect of the present invention, an additional reaction solvent may be used. Preferably the additional reaction solvent is a polar aprotic solvent, preferably dimethylsulfoxide (DMSO). Alternatively other solvents can be used. Preferred alternative solvents are other polar aprotic solvents, such as dimethylformamide (DMF), dimethylacetamide (DMA) or N-methyl-2-pyrrolidinone (NMP). Alternatively, hydrocarbon solvents can be used. Preferred hydrocarbon solvents are aromatic hydrocarbon solvents such as toluene or xylene.

Optionally, the intermediate compound, 2-chloro-6-diethanolamino-4,8-dipiperidino-pyrimido(5,4-d)pyrimidine, is isolated before being reacted with diethanolamine to form dipyridamole.

Irrespective of whether the reaction mixture is a neat mixture of the two reactants or an additional reaction solvent is used, preferably solvents are used during the work-up of the reaction. Preferred solvents used for the work-up are ethanol, toluene and water. Alternatively other solvents can be used. Preferred alternative solvents are other $C_1$-$C_6$ alkyl alcohols instead of ethanol and other hydrocarbon solvents instead of toluene, particularly aromatic hydrocarbon solvents such as xylene.

A particularly preferred process for the preparation of dipyridamole according to the present invention comprises the steps of:
(a) providing a mixture of 2,6-dichloro-4,8-dipiperidino-pyrimido(5,4-d)pyrimidine and diethanolamine;
(b) heating the mixture from step (a);
(c) adding a $C_1$-$C_6$ alkyl alcohol to the solution from step (b);
(d) adding a hydrocarbon solvent to the solution from step (c);
(e) adding water to the solution from step (d);
(f) cooling the mixture from step (e); and
(g) isolating the resulting solid.

Preferably this preferred process comprises the steps of:
(a) providing a mixture of 2,6-dichloro-4,8-dipiperidino-pyrimido(5,4-d)pyrimidine and diethanolamine;
(b) heating the mixture from step (a);
(c) adding ethanol to the solution from step (b);
(d) adding toluene to the solution from step (c);
(e) adding water to the solution from step (d);
(f) cooling the mixture from step (e); and
(g) isolating the resulting solid.

Preferably these preferred processes are carried out at a temperature below 130° C., preferably below 125° C.

Another particularly preferred process for the preparation of dipyridamole according to the present invention comprises the steps of:
(a) providing a mixture of 2,6-dichloro-4,8-dipiperidino-pyrimido(5,4-d)pyrimidine, diethanolamine and either a polar aprotic solvent or a hydrocarbon solvent;
(b) heating the mixture from step (a);
(c) adding a $C_3$-$C_8$ alkyl ketone or $C_3$-$C_8$ alkyl nitrile solvent to the solution from step (b);
(d) adding water to the solution from step (c);
(e) cooling the mixture from step (d);
(f) isolating the resulting 2-chloro-6-diethanolamino-4,8-dipiperidino-pyrimido(5,4-d) pyrimidine;
(g) preferably drying the solid;

(h) providing a mixture of 2-chloro-6-diethanolamino-4,8-dipiperidino-pyrimido(5,4-d) pyrimidine and diethanolamine;
(i) heating the mixture from step (h);
(j) adding a $C_1$-$C_6$ alkyl alcohol to the solution from step (i);
(k) adding a hydrocarbon solvent to the solution from step (j);
(l) adding water to the solution from step (k);
(m) cooling the mixture from step (l); and
(n) isolating the resulting solid.

Preferably this preferred process comprises the steps of:
(a) providing a mixture of 2,6-dichloro-4,8-dipiperidino-pyrimido(5,4-d)pyrimidine, diethanolamine and dimethylsulfoxide;
(b) heating the mixture from step (a);
(c) adding acetone to the solution from step (b);
(d) adding water to the solution from step (c);
(e) cooling the mixture from step (d);
(f) isolating the resulting 2-chloro-6-diethanolamino-4,8-dipiperidino-pyrimido(5,4-d) pyrimidine;
(g) drying the solid;
(h) providing a mixture of 2-chloro-6-diethanolamino-4,8-dipiperidinopyrimido(5,4-d) pyrimidine and diethanolamine;
(i) heating the mixture from step (h);
(j) adding ethanol to the solution from step (i);
(k) adding toluene to the solution from step (j);
(l) adding water to the solution from step (k);
(m) cooling the mixture from step (l); and
(n) isolating the resulting solid.

Preferably these preferred processes are carried out at a temperature below 130° C., preferably below 125° C.

Preferably any process according to the first aspect of the present invention provides dipyridamole in a molar yield of more than 60%, preferably more than 65%, preferably more than 70%, preferably more than 75%, preferably more than 80%, preferably more than 85%, from 2,6-dichloro-4,8-dipiperidino-pyrimido(5,4-d)pyrimidine.

Preferably any process according to the first aspect of the present invention provides dipyridamole on an industrial scale, preferably in batches of 100 g or more, 250 g or more, 500 g or more, 1 kg or more, 5 kg or more, 10 kg or more, 20 kg or more, or 50 kg or more.

Preferably any process according to the first aspect of the present invention is carried out without the use of any chromatography purification techniques.

A second aspect according to the present invention provides a process for the purification of dipyridamole comprising the steps of:
(a) heating a mixture of crude dipyridamole and diethanolamine to get a clear solution;
(b) adding a $C_1$-$C_6$ alkyl alcohol to the solution from step (a);
(c) adding a hydrocarbon solvent to the solution from step (b);
(d) adding water to the solution from step (c);
(e) cooling the mixture from step (d); and
(f) isolating the resulting solid.

Preferably the process according to the second aspect of the present invention comprises the steps of:
(a) heating a mixture of crude dipyridamole and diethanolamine to get a clear solution;
(b) adding ethanol to the solution from step (a);
(c) adding toluene to the solution from step (b);
(d) adding water to the solution from step (c);
(e) cooling the mixture from step (d); and
(f) isolating the resulting solid.

Preferably the process according to the second aspect of the present invention is carried out at a temperature below 90° C.

Preferably any process according to the second aspect of the present invention provides purified dipyridamole in a molar yield of more than 70%, preferably more than 80%, preferably more than 85%, preferably more than 90%, preferably more than 95%, from crude dipyridamole.

Preferably any process according to the second aspect of the present invention provides purified dipyridamole on an industrial scale, preferably in batches of 100 g or more, 250 g or more, 500 g or more, 1 kg or more, 5 kg or more, 10 kg or more, 20 kg or more, or 50 kg or more.

Preferably any process according to the second aspect of the present invention is carried out without the use of any chromatography purification techniques.

A third aspect according to the present invention provides dipyridamole prepared by a process according to the first or second aspect of the present invention. Preferably the dipyridamole according to the third aspect has a chemical purity of more than 99%, preferably more than 99.5%, more preferably more than 99.8%, and most preferably more than 99.9% (as measured by HPLC). Preferably the dipyridamole according to the third aspect comprises less than 0.1% of one or more of impurities A to F, preferably less than 0.05% of one or more of impurities A to F (as measured by HPLC) (see FIG. 1 for the structures of impurities A to F). Preferably the dipyridamole according to the third aspect comprises less than 0.1% of one or more of impurities A to G, preferably less than 0.05% of one or more of impurities A to G (as measured by HPLC) (see FIG. 1 for the structures of impurities A to G).

A fourth aspect according to the present invention provides dipyridamole with a chemical purity of greater than 99%, preferably greater than 99.5%, more preferably greater than 99.8%, and most preferably greater than 99.9% (as measured by HPLC). Preferably the dipyridamole according to the fourth aspect comprises less than 0.1% of one or more of impurities A to F, preferably less than 0.05% of one or more of impurities A to F (as measured by HPLC) (see FIG. 1 for the structures of impurities A to F). Preferably the dipyridamole according to the fourth aspect comprises less than 0.1% of one or more of impurities A to G, preferably less than 0.05% of one or more of impurities A to G (as measured by HPLC) (see FIG. 1 for the structures of impurities A to G).

A fifth aspect according to the present invention provides dipyridamole comprising less than about 0.1% of one or more of impurities A to F, preferably comprising less than about 0.05% of one or more of impurities A to F (as measured by HPLC) (see FIG. 1 for the structures of impurities A to F). The fifth aspect according to the present invention also provides dipyridamole comprising less than about 0.1% of one or more of impurities A to G, preferably comprising less than about 0.05% of one or more of impurities A to G (as measured by HPLC) (see FIG. 1 for the structures of impurities A to G). Preferably the dipyridamole according to the fifth aspect has a chemical purity of more than 99%, preferably more than 99.5%, more preferably more than 99.8%, and most preferably more than 99.9% (as measured by HPLC).

Preferably the dipyridamole according to the third, fourth and fifth aspects of the present invention is suitable for use in medicine, preferably for treating or preventing platelet aggregation and for preventing thrombosis, ischaemic stroke and transient ischaemic attacks.

A sixth aspect according to the present invention provides a pharmaceutical composition comprising dipyridamole according to the third, fourth or fifth aspect of the present invention. Preferably the pharmaceutical composition according to the sixth aspect comprises one or more pharmaceutically acceptable excipients. Optionally, the pharmaceutical composition according to the sixth aspect further comprises aspirin.

A seventh aspect according to the present invention provides the use of dipyridamole according to the third, fourth or fifth aspect of the present invention in the preparation of a medicament for treating or preventing platelet aggregation or for preventing thrombosis, ischaemic stroke or transient ischaemic attacks. Optionally, the medicament comprises dipyridamole and aspirin.

An eighth aspect according to the present invention provides a method for treating or preventing platelet aggregation or for preventing thrombosis, ischaemic stroke or transient ischaemic attacks, the method comprising administering to a patient in need thereof a therapeutically or prophylactically effective amount of dipyridamole according to the third, fourth or fifth aspect of the present invention or a therapeutically or prophylactically effective amount of the pharmaceutical composition according to the sixth aspect of the present invention. Preferably the patient is a mammal, preferably a human. Optionally, the method according to the eighth aspect comprises administering to a patient in need thereof a therapeutically or prophylactically effective amount of aspirin in addition to the therapeutically or prophylactically effective amount of dipyridamole.

BRIEF DESCRIPTION OF THE ACCOMPANYING FIGURES

FIG. 1 shows the structures of impurities A to G.

DETAILED DESCRIPTION OF THE INVENTION

The present invention provides improved processes for the preparation of dipyridamole, particularly for the preparation of highly pure dipyridamole. The improved processes are simple, inexpensive, good yielding and can be easily adopted for commercial production with a high degree of consistency and reproducibility.

The present inventors have surprisingly discovered that the use of lower reaction temperatures for the reaction of diethanolamine with 2,6-dichloro-4,8-dipiperidino-pyrimido(5,4-d)pyrimidine to form dipyridamole still affords complete reaction in a convenient time scale, but markedly reduces the levels of impurities formed in the reaction. The use of the lower reaction temperatures in the process according to the invention significantly controls the formation of impurities. Crude dipyridamole having a purity of greater than 98% was obtained by this process.

The present inventors have also developed a low temperature process of converting 2,6-dichloro-4,8-dipiperidino-pyrimido(5,4-d)pyrimidine to the mono-substituted product, 2-chloro-6-diethanolamino-4,8-dipiperidino-pyrimido(5,4-d)pyrimidine, by treating 2,6-dichloro-4,8-dipiperidino-pyrimido(5,4-d)pyrimidine with diethanolamine in a solvent. The mono-substituted intermediate is then converted to dipyridamole by reacting it with diethanolamine at low temperature. The isolation of 2-chloro-6-diethanolamino-4,8-dipiperidino-pyrimido(5,4-d)pyrimidine and further conversion to dipyridamole at lower temperature, in a process according to the invention, controls the formation of significant levels of impurities. Crude dipyridamole having a purity of greater than 98% was obtained by this process.

The levels of impurities in the crude product obtained in the processes of the present invention are significantly lower than in prior art processes. As a consequence, work-up and purification procedures become far more convenient than those disclosed in the prior art and dipyridamole with very high purity is easily and conveniently obtained.

A low temperature purification method to obtain dipyridamole with more than 99.8% purity has also been developed. The purification is achieved by using a novel solvent system, preferably comprising diethanolamine, ethanol, toluene and water. The reaction conditions and further purification method control the formation of all known and unknown impurities to well below acceptable levels, but employ temperatures much lower than prior art crystallization procedures.

In the processes according to the present invention 2,6-dichloro-4,8-dipiperidino-pyrimido(5,4-d)pyrimidine is added to diethanolamine. In preferred embodiments the mixture is heated to substantially dissolve the 2,6-dichloro-4,8-dipiperidino-pyrimido(5,4-d)pyrimidine. Preferably this temperature is about 110-125° C., most preferably about 113-115° C.

Therefore the processes of the present invention comprise improved and defined process parameters for the manufacturing of dipyridamole wherein the formation of impurities is precisely controlled and minimized. In addition, the processes of the present invention offer simpler work-up and/or purification procedures with optimum conditions for improved yield and quality with minimum contamination with process impurities. The improved processes can be easily adapted on commercial scale as efficient and convenient processes.

Advantageously, the processes of the present invention avoid column chromatography purification techniques, thereby making the processes simpler and more adaptable for large scale commercial production.

Further aspects of the present invention provide dipyridamole of greater than 99% purity (as measured by HPLC). Preferably the dipyridamole of the present invention has a purity of greater than 99.5%, more preferably greater than 99.8%, and most preferably greater than 99.9%.

The high quality dipyridamole prepared by the processes according to the present invention can be used for the preparation of a pharmaceutical composition to use in the manufacture of a medicament for anti-platelet therapy.

A preferred embodiment of the present invention, illustrated in Scheme 2, provides a process for the preparation of dipyridamole comprising reacting 2,6-dichloro-4,8-dipiperidino-pyrimido(5,4-d)pyrimidine with diethanolamine at 113-115° C. This reaction temperature is significantly lower than that used in the prior art processes to prepare dipyridamole.

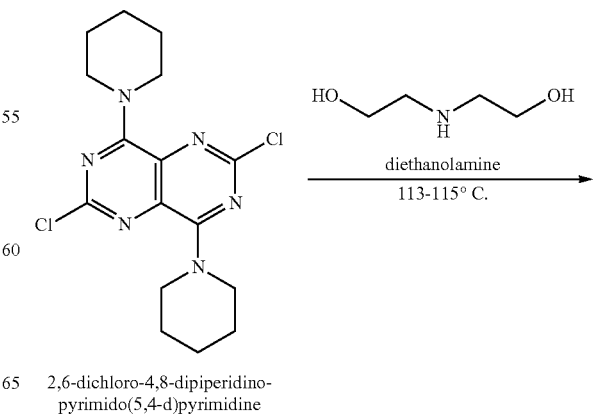

Scheme 2

2,6-dichloro-4,8-dipiperidino-pyrimido(5,4-d)pyrimidine

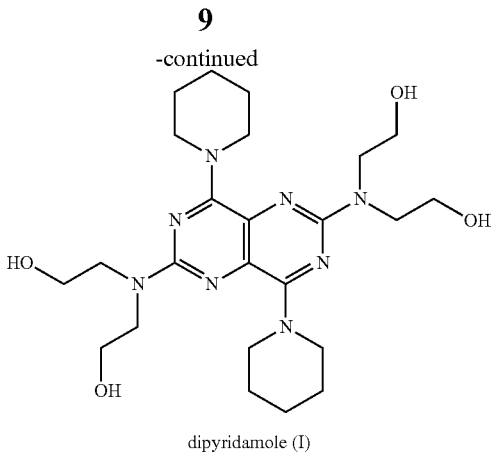

dipyridamole (I)

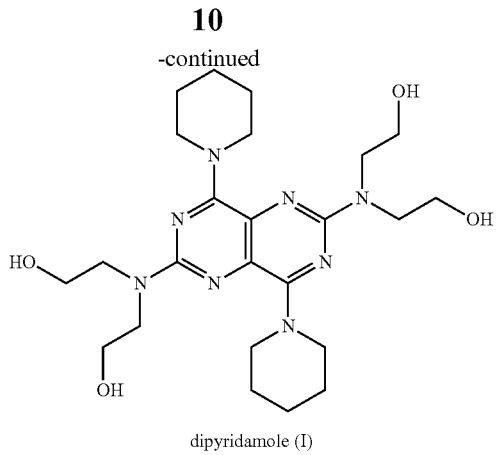

dipyridamole (I)

Another preferred embodiment of the present invention, illustrated in Scheme 3, also provides a process for the preparation of dipyridamole by the reaction of 2,6-dichloro-4,8-dipiperidino-pyrimido(5,4-d)pyrimidine with diethanolamine in dimethylsulfoxide at 120-125° C. to afford the monosubstituted intermediate, 2-chloro-6-diethanolamino-4,8-dipiperidino-pyrimido(5,4-d)pyrimidine, which is isolated and then further converted to dipyridamole by heating in diethanolamine at 113-115° C.

Although the solvent used in this preferred embodiment of the present invention is preferably dimethylsulfoxide (DMSO), other solvents can alternatively be used. Preferred alternative solvents are other polar aprotic solvents, such as dimethylformamide (DMF), dimethylacetamide (DMA) or N-methyl-2-pyrrolidinone (NMP). Alternatively, hydrocarbon solvents can be used. Preferred hydrocarbon solvents are aromatic hydrocarbon solvents such as toluene or xylene.

Scheme 3

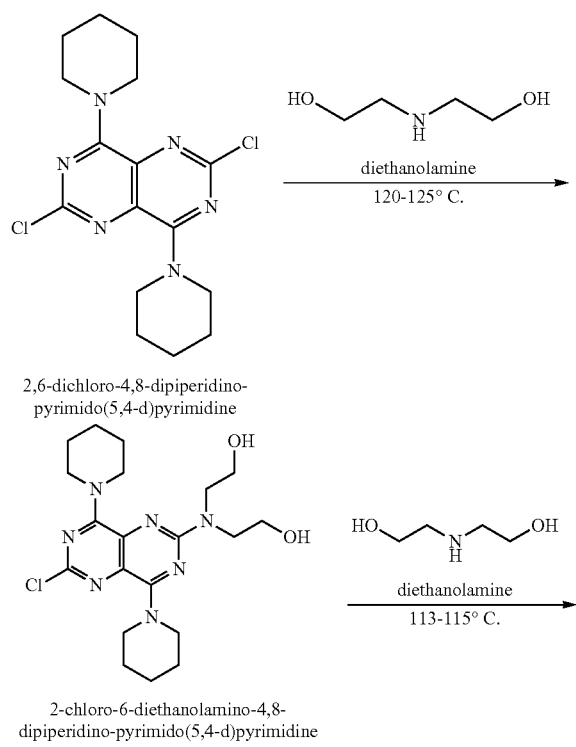

The crude dipyridamole obtained in preferred embodiments of the present invention or by any other processes, is preferably purified by using a novel solvent system consisting of diethanolamine, ethanol, toluene and water in a single step to afford highly pure dipyridamole.

In preferred embodiments of the present invention, pure dipyridamole is obtained substantially free of one or more of impurities A to G. The structures of impurities A to G are illustrated in FIG. 1.

A particularly preferred embodiment of the first aspect of the present invention comprises the following steps:
(a) providing a mixture of 2,6-dichloro-4,8-dipiperidino-pyrimido(5,4-d)pyrimidine and diethanolamine;
(b) heating the mixture from step (a);
(c) adding ethanol to the solution from step (b);
(d) adding toluene to the solution from step (c);
(e) adding water to the solution from step (d);
(f) cooling the mixture from step (e); and
(g) isolating the resulting solid.

Preferably the mixture from step (a) is heated to between about 110 to 125° C., preferably the mixture is heated to between about 113 to 115° C. Preferably ethanol is added to the mixture from step (b) at about 60-80° C., more preferably at about 75-80° C. Preferably toluene is added to the mixture from step (c) at about 60-80° C., more preferably at about 70-75° C. Preferably water is added to the mixture from step (d) at about 50-70° C., more preferably at about 60-65° C. Preferably the mixture from step (e) is cooled at about 20-40° C., more preferably at about 25° C. Preferably the solid from step (f) is isolated by filtration and preferably the solid is further washed, most preferably with water. Preferably the solid is further dried, preferably under vacuum. Although the two organic solvents used in this aspect of the present invention are preferably ethanol and toluene, other solvents can alternatively be used. Preferred alternative solvents are other $C_1$-$C_6$ alkyl alcohols instead of ethanol and other hydrocarbon solvents instead of toluene, particularly aromatic hydrocarbon solvents such as xylene.

Another preferred embodiment of the first aspect of the present invention comprises the following steps:
(a) providing a mixture of 2,6-dichloro-4,8-dipiperidino-pyrimido(5,4-d)pyrimidine, diethanolamine and dimethylsulfoxide;
(b) heating the mixture from step (a);
(c) adding acetone to the solution from step (b);
(d) adding water to the solution from step (c);
(e) cooling the mixture from step (d);
(f) isolating the resulting solid 2-chloro-6-diethanolamino-4,8-dipiperidino-pyrimido(5,4-d)pyrimidine;

(g) drying the solid;
(h) providing a mixture of 2-chloro-6-diethanolamino-4,8-dipiperidino-pyrimido(5,4-d)pyrimidine and diethanolamine;
(i) heating the mixture from step (h);
(j) adding ethanol to the solution from step (i);
(k) adding toluene to the solution from step (j);
(l) adding water to the solution from step (k);
(m) cooling the mixture from step (l); and
(n) isolating the resulting solid.

Preferably the mixture from step (a) is heated to between about 110 and 130° C., more preferably the mixture is heated to about 120-125° C. Preferably acetone is added to the mixture from step (b) at about 45-60° C., more preferably at about 55-60° C. Preferably water is added to the mixture from step (c) at about 50-70° C., more preferably at about 55-60° C. Preferably the mixture from step (d) is cooled at about 20-40° C., more preferably at about 25° C. Preferably the resultant solid from step (e) is isolated in step (f) by filtration and preferably the solid is further washed, most preferably with water. Preferably the solid is further dried, preferably under vacuum. Preferably the mixture from step (h) is heated to between about 110 and 125° C., more preferably the mixture is heated to about 113-115° C. Preferably ethanol is added to the mixture from step (i) at about 60-80° C., more preferably at about 75-80° C. Preferably toluene is added to the mixture from step (j) at about 60-80° C., more preferably at about 70-75° C. Preferably water is added to the mixture from step (k) at about 50-70° C., more preferably at about 60-65° C. Preferably the mixture from step (l) is cooled at about 20-40° C., more preferably at about 25° C. Preferably the resultant solid from step (m) is isolated by filtration and preferably the solid is further washed, most preferably with water. Preferably the solid is further dried, preferably under vacuum. Although the four organic solvents used in this aspect of the present invention are preferably DMSO, acetone, ethanol and toluene, other solvents can alternatively be used. Preferred alternative solvents are: instead of DMSO other polar aprotic solvents such as dimethylformamide (DMF), dimethylacetamide (DMA) or N-methyl-2-pyrrolidinone (NMP) or hydrocarbon solvents such as aromatic hydrocarbon solvents such as toluene or xylene; instead of acetone other $C_3$-$C_8$ alkyl ketones or alkyl nitriles such as acetonitrile; instead of ethanol other $C_1$-$C_6$ alkyl alcohols; and instead of toluene other hydrocarbon solvents, particularly aromatic hydrocarbon solvents such as xylene.

A preferred embodiment of the second aspect of the present invention comprises the following steps:
(a) heating a mixture of crude dipyridamole and diethanolamine to obtain a clear solution;
(b) adding ethanol to the solution from step (a);
(c) adding toluene to the solution from step (b);
(d) adding water to the solution from step (c);
(e) cooling the mixture from step (d); and
(f) isolating the resulting solid.

Preferably the mixture from step (a) is heated to between about 60 and 90° C., more preferably the mixture is heated to about 75-80° C. Preferably ethanol is added to the mixture from step (a) at about 60-80° C., preferably at about 75-80° C. Preferably toluene is added to the mixture from step (b) at about 60-80° C., more preferably at about 70-75° C. Preferably water is added to the mixture from step (c) at about 50-75° C., more preferably at about 70-75° C. Preferably the mixture from step (d) is cooled at about 20-40° C., more preferably at about 25° C. Preferably the resultant solid from step (e) is isolated by filtration and preferably the solid is further washed, most preferably with water. Preferably the solid is further dried, preferably under vacuum. Although the two organic solvents used in this aspect of the present invention are preferably ethanol and toluene, other solvents can alternatively be used. Preferred alternative solvents are other $C_1$-$C_6$ alkyl alcohols instead of ethanol and other hydrocarbon solvents instead of toluene, particularly aromatic hydrocarbon solvents such as xylene.

A further aspect of the present invention provides dipyridamole comprising less than about 0.1%, preferably less than about 0.05% of impurities A to G and/or any other unknown impurities.

The dipyridamole prepared by the improved processes according to the present invention is >99.8% pure by HPLC analysis and more preferably >99.9% pure by HPLC analysis.

The dipyridamole prepared by the improved processes according to the present invention can be easily converted into any suitable salt if required. The highly pure dipyridamole can be converted into a salt, if required, with a chemical purity >99.9% (as measured by HPLC). Typical salts are preferably pharmaceutically acceptable addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic acid) or amino acids (for example, ornithinic, glutamic or aspartic acid). The acid addition salt may be a mono-, di- or tri-acid addition salt.

Further details of the invention are illustrated below in the following non-limiting examples.

EXAMPLES

As used hereinafter in the examples, the term '1 vol' means that for each gram of starting material 1 ml of solvent is used. The terms '2 vol', '3 vol' etc. are used accordingly.

Example 1

Preparation of Crude Dipyridamole

Diethanolamine (10 vol) and 2,6-dichloro-4,8-dipiperidino-pyrimido(5,4-d)pyrimidine (1 eq) were mixed at 25-30° C., stirred for 10 minutes and then heated at 113-115° C. for 45-48 hours. After completion of the reaction, the mixture was cooled to 75-80° C. Ethanol (5 vol) was added at 75-80° C. and the mixture was stirred at 75-80° C. for 10 minutes. Toluene (10 vol) was added at 70-75° C. and the mixture was stirred at 70-75° C. for 15 minutes. Purified water (15 vol) was added at 70-75° C. and the mixture was stirred at 60-65° C. for 30 minutes. The mixture was then cooled and stirred at 25-30° C. for 30 minutes. The precipitated solid was filtered and washed with purified water (2×5 vol) before drying at 75-80° C. under reduced pressure afforded crude dipyridamole as a yellow crystalline solid.

Yield (w/w)=80-85%
Yield (molar)=58-62%
HPLC purity≥98%

Example 2

Stage 1: Preparation of 2-chloro-6-diethanolamino-4,8-dipiperidino-pyrimido(5,4-d)pyrimidine Diethanolamine (3 eq) and 2,6-dichloro-4,8-dipiperidino-pyrimido(5,4-d)pyrimidine (1 eq) were added to dimethylsulfoxide (10 vol) at 25-30° C., stirred for 10 minutes and then heated at 120-125° C. for 4-5 hours. After completion of the reaction, the reaction mixture was cooled to 55-60° C. Acetone (5 vol) was added at 55-60° C. and the mixture was stirred at 55-60° C. for 10 minutes. Purified water (15 vol) was added at 55-60° C. and the mixture was stirred at 50-55° C. for 15 minutes. The mixture was cooled to 25-30° C. and stirred at 25-30° C. for 30 minutes. The precipitated solid was filtered, washed with purified water (2×5 vol) and dried at 75-80° C. under reduced pressure to afford crude 2-chloro-6-diethanolamino-4,8-dipiperidino-pyrimido(5,4-d)pyrimidine as a yellow crystalline solid.

Yield (w/w)=110-120%
Yield (molar)=93-100%
HPLC purity≥96%

Stage 2: Preparation of Crude Dipyridamole

Diethanolamine (10 vol) and 2-chloro-6-diethanolamino-4,8-dipiperidino-pyrimido(5,4-d)pyrimidine (1 eq) were mixed at 25-30° C., stirred for 10 minutes and then heated at 113-115° C. for 45-48 hours. After completion of the reaction, the mixture was cooled to 75-80° C. Ethanol (5 vol) was added and the mixture was stirred at 75-80° C. for 10 minutes. Toluene (10 vol) was added and the mixture was stirred at 70-75° C. for 15 minutes. Purified water (15 vol) was added and the mixture was stirred at 60-65° C. for 30 minutes. The mixture was then cooled to 25-30° C. and stirred for 30 minutes. The precipitated solid was filtered, washed with purified water (2×5 vol) and dried at 75-80° C. under reduced pressure to afford crude dipyridamole as a yellow crystalline solid.

Yield (w/w)=95-97%
Yield (molar)=82-84%
HPLC purity≥98%

Example 3

Crystallization of Crude Dipyridamole

Crude dipyridamole (1 eq) and diethanolamine (8 vol) were stirred together at 25-30° C. for 10 minutes and then heated to about 80° C. for 10 minutes. The clear solution was cooled to 75-80° C., ethanol (5 vol) was added and the mixture was stirred at 75-80° C. for 10 minutes. Toluene (10 vol) was added and the mixture was stirred at 70-75° C. for 15 minutes. The mixture was cooled to 25-30° C., stirred at 25-30° C. for 10 minutes and filtered. The filtrate was heated to 70-75° C. for 10 minutes, purified water (15 vol) was added and the mixture was stirred at 60-65° C. for 30 minutes before cooling to 25-30° C. with stirring for 30 minutes. The precipitated solid was filtered, washed with purified water (2×5 vol) and dried at 75-80° C. under reduced pressure to afford dipyridamole as a yellow crystalline solid.

Yield (w/w and molar)=90-95%
HPLC purity≥99.9%

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A process for the preparation of dipyridamole comprising reacting 2,6-dichloro-4,8-dipiperidino-pyrimido(5,4-d)pyrimidine with diethanolamine at a temperature below 130° C.

2. The process according to claim 1, wherein the reaction temperature is:
 (i) between about 100° C. and below 130° C.; and/or
 (ii) between about 100° C. and about 125° C.; and/or
 (iii) between about 110° C. and about 125° C.; and/or
 (iv) between about 110° C. and about 120° C.; and/or
 (v) between about 110° C. and about 115° C.; and/or
 (vi) between about 113° C. and about 115° C.

3. The process according to claim 1, wherein the reaction mixture is a neat mixture of the two reactants, 2,6-dichloro-4,8-dipiperidino-pyrimido(5,4-d)pyrimidine and diethanolamine, with no additional reaction solvent.

4. The process according to claim 3, wherein the 2,6-dichloro-4,8-dipiperidino-pyrimido(5,4-d)pyrimidine is dissolved in the diethanolamine.

5. The process according to claim 1, wherein an additional reaction solvent is used.

6. The A process according to claim 5, wherein the additional reaction solvent is a polar aprotic solvent.

7. A The process according to claim 6, wherein the solvent is dimethylsulfoxide.

8. The process according to claim 5, wherein the intermediate compound, 2-chloro-6-diethanolamino-4,8-dipiperidino-pyrimido(5,4-d)pyrimidine, is isolated before being reacted with diethanolamine to form dipyridamole.

9. A process according to claim 1, comprising the steps of:
 (a) providing a mixture of 2,6-dichloro-4,8-dipiperidino-pyrimido(5,4-d)pyrimidine and diethanolamine;
 (b) heating the mixture from step (a);
 (c) adding a $C_1$-$C_6$ alkyl alcohol to the solution from step (b);
 (d) adding a hydrocarbon solvent to the solution from step (c);
 (e) adding water to the solution from step (d);
 (f) cooling the mixture from step (e); and
 (g) isolating the resulting solid.

10. A process according to claim 1, comprising the steps of:
 (a) providing a mixture of 2,6-dichloro-4,8-dipiperidino-pyrimido(5,4-d)pyrimidine, diethanolamine and either a polar aprotic solvent or a hydrocarbon solvent;
 (b) heating the mixture from step (a);
 (c) adding a $C_3$-$C_8$ alkyl ketone or $C_3$-$C_8$ alkyl nitrile solvent to the solution from step (b);
 (d) adding water to the solution from step (c);
 (e) cooling the mixture from step (d);
 (f) isolating the resulting 2-chloro-6-diethanolamino-4,8-dipiperidino-pyrimido(5,4-d) pyrimidine;
 (g) preferably drying the solid;
 (h) providing a mixture of 2-chloro-6-diethanolamino-4,8-dipiperidino-pyrimido(5,4-d) pyrimidine and diethanolamine;
 (i) heating the mixture from step (h);
 (j) adding a $C_1$-$C_6$ alkyl alcohol to the solution from step (i);
 (k) adding a hydrocarbon solvent to the solution from step (j);
 (l) adding water to the solution from step (k);
 (m) cooling the mixture from step (l); and
 (n) isolating the resulting solid.

11. A process according to claim 1, further comprising for the purification of dipyridamole comprising the steps of:
 (a) heating a mixture of crude dipyridamole and diethanolamine to get a clear solution;
 (b) adding a $C_1$-$C_6$ alkyl alcohol to the solution from step (a);
 (c) adding a hydrocarbon solvent to the solution from step (b);
 (d) adding water to the solution from step (c);
 (e) cooling the mixture from step (d); and
 (f) isolating the resulting solid.

* * * * *